US012636639B2

(12) United States Patent
Tahir

(10) Patent No.: US 12,636,639 B2
(45) Date of Patent: May 26, 2026

(54) NANOCOMPOSITE MATERIAL COMPRISING BIO-SLUDGE OR BIOCHAR, METHOD FOR ITS PREPARATION AND APPLICATION IN PHOTOCATALYTIC CO2 REDUCTION

(71) Applicant: United Arab Emirates University, Al Ain (AE)

(72) Inventor: Muhammad Tahir, Al Ain (AE)

(73) Assignee: UNITED ARAB EMIRATES UNIVERSITY, Al-Ain (AE)

(*) Notice: Subject to any disclaimer, the term of this patent is extended or adjusted under 35 U.S.C. 154(b) by 0 days.

(21) Appl. No.: 18/755,128

(22) Filed: Jun. 26, 2024

(65) Prior Publication Data

US 2026/0001057 A1 Jan. 1, 2026

(51) Int. Cl.

| | |
|---|---|
| ***B01J 21/18*** | (2006.01) |
| ***B01J 21/06*** | (2006.01) |
| ***B01J 35/39*** | (2024.01) |
| ***B01J 37/00*** | (2006.01) |
| ***B01J 37/04*** | (2006.01) |
| ***B01J 37/08*** | (2006.01) |
| ***C01B 32/05*** | (2017.01) |
| ***C01B 32/40*** | (2017.01) |
| ***C01G 23/053*** | (2006.01) |
| ***C07C 1/02*** | (2006.01) |

(52) U.S. Cl.

CPC ............. *B01J 21/18* (2013.01); *B01J 21/063* (2013.01); *B01J 35/39* (2024.01); *B01J 37/0036* (2013.01); *B01J 37/04* (2013.01); *B01J 37/08* (2013.01); *C01B 32/05* (2017.08); *C01B 32/40* (2017.08); *C01G 23/053* (2013.01); *C07C 1/02* (2013.01); *C07C 2521/06* (2013.01)

(58) Field of Classification Search

None

See application file for complete search history.

(56) References Cited

U.S. PATENT DOCUMENTS

| | | | | |
|---|---|---|---|---|
| 2004/0105810 A1* | 6/2004 | Ren | C01G 17/00 | 423/592.1 |
| 2004/0182792 A1* | 9/2004 | Subrahmanyam | C02F 1/725 | 210/198.1 |
| 2014/0107371 A1* | 4/2014 | Bakker | B01J 37/06 | 558/414 |
| 2019/0055168 A1* | 2/2019 | Wang | C05F 5/002 | |
| 2023/0270555 A1* | 8/2023 | Rahimi | A61F 2/3094 | 427/2.1 |

(Continued)

OTHER PUBLICATIONS

Cai et al, Titanium dioxide-coated biochar composites as adsorptive and photocatalytic degradation materials for the removal of aqueous organic pollutants, J Chem Technol Biotechnol, 93, 783-791 (Year: 2017).*

(Continued)

*Primary Examiner* — Stefanie J Cohen

(74) *Attorney, Agent, or Firm* — MH2 Technology Law Group, LLP

(57) ABSTRACT

The present disclosure relates to bio-sludge, and biochar based nanocomposite material, and preparation methods thereof. In particular, the present disclosure relates to a bio-sludge and biochar based $TiO_2$ nanocomposite materials for photocatalytic $CO_2$ reduction and a preparation method thereof.

11 Claims, 7 Drawing Sheets

(56) References Cited

U.S. PATENT DOCUMENTS

2024/0109051 A1* 4/2024 Ma ........................ B01J 20/3085
2024/0174566 A1* 5/2024 Li ........................ C04B 14/305

OTHER PUBLICATIONS

Wang et al, Hierarchically structured two-dimensional magnetic microporous biochar derived from hazelnut shell toward effective removal of p-arsanilic acid, (Year: 2021).*
Liu et al, Boosting electron kinetics of anatase TiO2 with carbon nanosheet for efficient photo-reforming of xylose into biomass-derived organic acids, Journal of alloys and compounds, 906 (Year: 2022).*

* cited by examiner

NANOCOMPOSITE MATERIAL COMPRISING BIO-SLUDGE OR BIOCHAR, METHOD FOR ITS PREPARATION AND APPLICATION IN PHOTOCATALYTIC CO2 REDUCTION

TECHNICAL FIELD

The present disclosure relates to nanocomposite material comprising bioderived sludge (hereinafter referred to as bio-sludge), or bio-sludge char (hereinafter referred to as biochar) as cocatalyst, and preparation methods thereof. In particular, the present disclosure relates to nanocomposite material comprising bio-sludge or biochar and $TiO_2$ for photocatalytic $CO_2$ reduction and a preparation method thereof.

BACKGROUND

Carbon dioxide ($CO_2$) is a prominent greenhouse gas, which significantly contributes to climate change by trapping heat in the atmosphere, leading to global warming and associated environmental disruptions. Human activities, including the combustion of fossil fuels (coal and natural gas) for energy, industrial processes, deforestation, and certain agricultural practices, are the primary sources of $CO_2$ emissions. The conversion of $CO_2$ into valuable chemicals and fuels through photocatalytic processes offers a promising solution. It is very important to develop systems to capture $CO_2$ from the atmosphere and reduce it to useful hydrocarbons which we use as a fuel instead of fossil fuel. This technique helps to solve the global warming issue and energy shortage simultaneously.

Photocatalytic $CO_2$ reduction using solar energy presents an innovative approach to combat climate change by converting carbon dioxide, a greenhouse gas, into useful fuels and chemicals using renewable solar energy.

Photocatalysts, while showing promise, are often limited by factors such as low efficiency, poor selectivity, and high recombination rates of photoinduced electron-hole pairs. Many efforts have been made to synthesize and modify different photocatalysts for the photocatalyst reduction of $CO_2$ but their efficiency is still not enough for practical use on a commercial level. The main reasons are deficiency in the charge transfer channel and the active sites not being sufficient to fulfil the requirement for $CO_2$ reduction. It is a big task to synthesize such efficient materials for $CO_2$ photocatalytic reduction which have earned more light to perform better results. To resolve this problem, many techniques have been used to further activate the electronic deposition such as atomic doping and metal deposition. Some emerging concepts and platforms are facilitating the design of cocatalysts of $TiO_2$ in a cost-effective way, with good quantum efficiency for expanding the $TiO_2$'s photocatalytic applications.

Titanium dioxide ($TiO_2$) is deeply investigated due to its photostability, high performance, proper band edge positions, low cost, and environmentally friendly hydrogen synthesis utilizing solar radiation. However, one of the major challenges with $TiO_2$ is the recombination of photogenerated charge carriers. The other primary concern with $TiO_2$ as a photocatalyst in solar energy converters is that it absorbs only a small fraction of the most energetic amount of the solar spectral range. Although numerous distinct strategies have been tried to boost $TiO_2$ photoactivity in the visible range by doping it with p-block elements, the solution may be found only by using various semiconductor oxides.

Traditional $TiO_2$ photocatalysts suffer from large band gaps and limited light absorption, hindering their effectiveness in $CO_2$ conversion. Despite efforts to enhance their performance through composite structures and doping strategies, these materials fall short of achieving the desired level of efficiency and/or selectivity. They suffer from drawbacks such as limited efficiency, reduced photostability, shorter catalytic activity, and considerable costs associated with their maintenance and replacement. Some may exhibit instability or deactivation over time, necessitating frequent regeneration or replacement, which adds complexity to their handling and increases overall operational costs.

In recent years, biochar-based photocatalysts (BCPs) have gained a lot of interest in the environmental sphere. There has been a lot of investigation on the adsorption properties of biochar and the photocatalytic $H_2$ production mechanism of $TiO_2$, but there hasn't been enough study on the cross-linked framework of particulate carbon materials (biochar) and $TiO_2$. Furthermore, the combinatorial mechanism of the photocatalytic process based on the research of biochar metallic element's role and contribution to the cross-linked structure and hydrogen production performance has not been investigated.

Therefore, there is a need to address the one or more limitations associated with existing catalysts used in the photocatalytic processes of $CO_2$ reduction.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present disclosure provides bio-sludge, or biochar based $TiO_2$ nanocomposite materials for photocatalytic $CO_2$ reduction and a preparation method thereof. The nanocomposite of the present invention addresses one or more limitations associated with existing catalysts used in the photocatalytic reduction of $CO_2$.

In one aspect, the present disclosure provides a nanocomposite material comprising 2D/0D bio-sludge or biochar/$TiO_2$.

In another aspect, the present disclosure provides a method for producing the bio-sludge or biochar/$TiO_2$ nanocomposite material by combining the bio-sludge or the biochar with $TiO_2$ nanoparticles using a sol-gel process and/or self-assembly of the particles through physical mixing.

The method comprises the steps of:

a) preparing a suspension of $TiO_2$ particles or its precursor in an alcoholic solvent;

b) preparing a suspension of bio-sludge or biochar in an alcoholic solvent;

c) mixing the suspensions obtained in step a), and step b) to obtain a suspension of the $TiO_2$ nanoparticles or its precursor and bio-sludge or biochar particles; and d) drying and/or calcining the suspension obtained in step c).

In yet another aspect, the present disclosure provides bio-sludge or a biochar/$TiO_2$ nanocomposite material prepared by the process of the preceding aspect.

In yet another aspect, the present disclosure provides a process for photocatalytic reduction of $CO_2$ using the bio-sludge or a biochar/$TiO_2$ nanocomposite material of the present disclosure. The process comprises contacting a feed comprising $CO_2$ and at least one sacrificial compound with a nanocomposite provided in the preceding aspect(s), in a photocatalytic system; and irradiating the photocatalyst with at least one irradiation source.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where:

DETAILED DESCRIPTION

Figure 1:
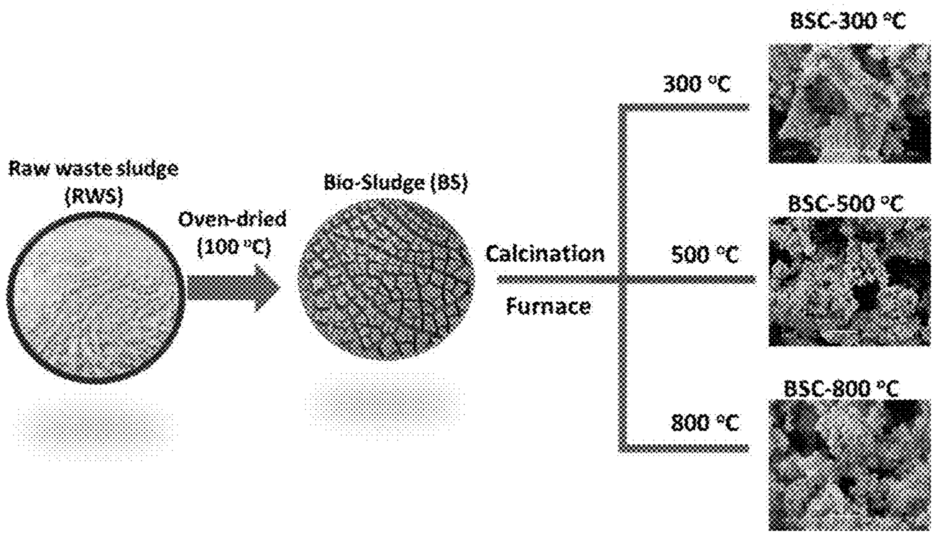
FIG. 1 shows schematic illustration for the synthesis of BS and bioderived char (BSC) at different temperatures.

The present disclosure provides bio-sludge or biochar based $TiO_2$ nanocomposite materials for photocatalytic $CO_2$ reduction and a preparation method thereof. The nanocomposites of the present invention address one or more limitations associated with existing catalysts used in the photocatalytic processes of $CO_2$ reduction.

In one embodiment of the present disclosure, the present disclosure leverages the unique properties of bio-sludge, and biochar as cocatalysts for enhancing the photocatalytic activity of $TiO_2$ towards $CO_2$ reduction. The present disclosure provides a low-cost sustainable and environment friendly nanocomposite material with high efficiency, capable of harvesting solar energy for low-carbon energy applications.

The present disclosure can be understood more readily by reference to the following description taken in connection with the accompanying Figures and Examples, all of which form a part of this disclosure.

At the very outset of the detailed description, it may be understood that the ensuing description only illustrates a particular form of this invention. However, such a particular form is only an exemplary embodiment, and without intending to imply any limitation on the scope of this invention. Accordingly, the description is to be understood as an exemplary embodiment and teaching of invention and not intended to be taken restrictively.

Before the present disclosure or methods of the present disclosure are described in greater detail, it is to be understood that the specific products, methods, processes, conditions or parameters, are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. Where the stated range includes one or both of the limits, ranges excluding either or both of those included limits are also included in the methods. Certain ranges are presented herein with numerical values being preceded by the term "about." The term "about" is used herein to provide literal support for the exact number that it precedes, as well as a number that is near to or approximately the number that the term precedes. For example, "about" can mean within one or more standard deviations, or within ±30%, 25%, 20%, 15%, 10% or 5% of the stated value.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or composites/scaffolds.

The articles "a" and "an" are used herein to refer to one or to more than one (i.e., to at least one) of the grammatical object of the article. By way of example, "an element" means one element or more than one element.

As used herein, the term "comprises", "comprising", or "comprising of" is generally used in the sense of include, that is to say permitting the presence of one or more features or components. The term "comprises", "comprising", or "comprising of" when placed before the recitation of steps in a process or method means that the process or method encompasses one or more steps that are additional to those expressly recited, and that the additional one or more steps may be performed before, between, and/or after the recited steps.

Reference throughout this specification to "certain embodiments", "further embodiments", "specific embodiments", "further specific embodiment", "one embodiment", "a non-limiting embodiment", "an exemplary embodiment", "some instances", or "further instances", means that a particular feature, structure or characteristic described in connection with the embodiment may be included in at least one embodiment of the present disclosure.

As used herein, the terms 'include', 'have', 'comprise', 'contain' etc. or any form of said terms such as 'having', 'including', 'containing', 'comprising' or 'comprises' are inclusive and will be understood to imply the inclusion of a stated element, integer or step, or group of elements, integers or steps, but not the exclusion of any other element, integer or step, or group of elements, integers or steps.

The use of any and all examples, or exemplary language (e.g., "such as") provided with respect to certain embodiments herein is intended merely to better illustrate the disclosure and does not pose a limitation on the scope of the disclosure otherwise claimed.

As used herein, the term "invention", "present invention", "disclosure" or "present disclosure" as used herein is a non-limiting term and is not intended to refer to any single embodiment of the particular invention but encompasses all possible embodiments as described in the specification.

The terms "process(es)" and "method(s)" are considered interchangeable within this disclosure.

In one aspect, the present disclosure provides a nanocomposite material comprising 2D/0D bio-sludge or sludge biochar/$TiO_2$.

In an embodiment, the binary 2D/0D bio-sludge or biochar/$TiO_2$ nanocomposite material has a structure where the bio-sludge or the biochar has a two-dimensional (2D) structure, while the $TiO_2$ nanoparticles are zero dimensional (0D). The nanocomposite has a hierarchical nanotexture with one or more layers.

By hierarchical nanostructures, it is meant to say that the composites have well-ordered nanoscale subunits with specific (0D, and 2D) dimensions. The structure includes hierarchical porous nanotexture over different lengths leading to a variety of desirable functionalities for a large number of applications.

In an embodiment, the 0D $TiO_2$ nanoparticles are dispersed in or on to the bio-sludge and biochar layered structure. The bio-sludge/biochar loading in the composite is in the range from about 1 wt % to about 10 wt %, from about 1 wt % to 5 wt %, or about 3 wt % to the total weight of the nanocomposite.

In an embodiment, the nanocomposite has different scales of pores or active sites. The nanocomposite may be in the form of more than one layer with multiple levels of porosity or spatial organization. In a specific embodiment, an alternate deposition of $TiO_2$ and bio-sludge, or biochar may happen to create multilayered structures with hierarchical properties.

In a further specific embodiment, the nanocomposite of the present invention is a supported composite or an unsupported composite. The nanocomposite can be supported on materials such as carbon nanotubes or mesoporous materials. These support structures can provide additional stability and surface area for the cocatalyst. In a specific embodiment, the nanocomposite photocatalyst is supported on a substrate. The support may be composed of various materials, such as ceramic, graphene, metal, metal oxides, metal alloys, polymers, etc.

The 2D/0D bio-sludge or biochar/$TiO_2$ nanocomposite material is characterized by XRPD pattern, Raman spectra, morphology, X-ray photoelectron spectroscopy (XPS), UV-visible absorption, Photoluminescence (PL) analysis.

The 2D/0D bio-sludge or biochar/$TiO_2$ nanocomposite material possess superior characteristics, including increased pore volume, higher visible light absorbance, and charge separation efficiency when compared to $TiO_2$. The nanocomposites showcase a synergistic enhancement, manifesting a collective improvement in surface area, higher light absorbance and bigger band gap, pore volume, and stability relative to $TiO_2$, and promote carrier lifetime. The bio-sludge or a biochar/$TiO_2$ nanocomposite material of the present disclosure is useful for achieving higher solar energy conversion efficiency, $CO_2$ conversion efficiency, and/or stability across multiple cycles, with CO, $CH_4$, and $H_2$ as the main products.

In another aspect, the present disclosure provides a method for producing a nanocomposite material comprising bio-sludge or biochar/$TiO_2$. The method comprises combining the bio-sludge or biochar with $TiO_2$ by a sol-gel process and/or self-assembly of the particles through physical mixing.

In an embodiment, the method comprises the steps of:

a) preparing a suspension of $TiO_2$ particles or its precursor in an alcoholic solvent;

b) preparing a suspension of bio-sludge or biochar in an alcoholic solvent;

c) mixing the suspensions obtained in step a), and step b) to obtain a suspension of the $TiO_2$ nanoparticles or its precursor and bio-sludge or biochar particles; and d) drying and/or calcining the suspension obtained in step c).

Step a)

The suspension of $TiO_2$ particles or its precursor for the purposes of the present invention may be arrived at by preparing a suspension of $TiO_2$ particles or its precursor in an alcoholic solvent selected from a group comprising methanol, ethanol, 2-propanol, and a mixture thereof.

In an embodiment, the $TiO_2$ particles employed for the purposes of the present invention is prepared by a process comprising the steps of:

i) mixing a titanium precursor and an alcohol solvent to obtain a solution;

ii) adding an acid to the solution of step i);

iii) stirring to obtain a suspension of $TiO_2$ particles in a hydrated form; and iv) grinding and drying/calcining the suspension to obtain the $TiO_2$ particles.

Step i):

The titanium precursor employed in step i) comprises a titanium alkoxide, titanium (IV) halide, titanium (IV) oxysulfate, titanium (IV) nitrate, titanium (IV) oxide, titanium (IV) acetylacetonate, titanium (IV) sulfate etc. or mixture thereof.

In a specific embodiment, the titanium precursor is titanium alkoxide selected from titanium (IV) isopropoxide, titanium n-butoxide and titanium ethoxide. In a further specific embodiment, the titanium precursor comprises titanium (IV) isopropoxide.

The alcohol solvent may be selected from a group comprising methanol, ethanol, propanol, 2-propanol, butanol, and a mixture thereof. In a specific embodiment, the alcohol solvent comprises methanol, or 2-propanol.

The ratio of the titanium precursor to the alcohol solvent is from about 1:1 to about 1:10, preferably from about 1:2 to about 1:5.

In certain embodiments, the mixing is done at a temperature of about 10° C. to about 50° C. for about 5 min to about 20 hours. In some embodiments, the mixing is done at room temperature for about 5 min to about 45 min, about 10 min to about 45 min, or about 15 min to about 45 min. In some embodiments, the stirring is done at room temperature for about 15 min, about 20 min, about 25 min, about 30 min, about 35 min, about 40 min, or about 45 min. In some instances, the stirring is done at room temperature for about 30 min.

Step ii):

The acid employed for the purposes of this step is an organic acid comprising acetic acid, or an inorganic acid such as hydrochloric acid, sulfuric acid, nitric acid, etc., or a mixture thereof. In a specific embodiment, the organic acid comprises acetic acid in a quantity of 1 to 5 ml.

The acid may be optionally dissolved in an alcohol solvent. The alcohol solvent employed can be the same as employed in step i) or different. The ratio of the acid to the alcohol solvent is from about 0.1:1 to about 0.1:10, preferably, about 0.5 to 1.0 to 0.8:1.0

In certain embodiments, the stirring is done at a temperature of about 10° C. to about 50° C. for about 1 hour to about 20 hours, or from about 1 hour to about 15 hours.

Step iii):

Step iii) comprises stirring to obtain a suspension of $TiO_2$ particles in a hydrated form. In certain embodiments, the stirring is done at a temperature of about 10° C. to about 50° C. for about 1 to 20 hours.

In a specific embodiment, the suspension (titanium sol) is obtained by hydrolyzing TTIP (Titanium (IV) isopropoxide) in acetic acid (1 M) using 10 mL of TTIP dissolved in 2-propanol.

In a specific embodiment, the suspension in step iii) has $TiO_2$ in hydrated form.

Step iv):

Grinding and drying/calcining is carried at high temperatures of about 100° C. to about 500° C. for about 2 h to about 32 h.

Grinding of $TiO_2$ (titanium dioxide) particles is a crucial step in the preparation of $TiO_2$-based materials to achieve desired particle size and morphology, which in turn can significantly affect their photocatalytic properties and applications. Grinding can be carried out in a ball mill, using wet grinding, jet milling etc.

The ground material is dried and/or calcined. Any drying technique, such as normal over drying, micro-oven drying, and the like, may be employed. Drying may be carried out at temperatures of about 100 to 500° C.

The ground material may be subjected to calcination after initial drying or directly at a temperature of about 300° C. to about 800° C. In certain embodiments, the calcining is carried out at about 500° C.

Step b):

The step of preparing a suspension of bio-sludge or biochar in an alcoholic solvent involves an alcoholic solvent selected from a group comprising methanol, ethanol, propanol, 2-propanol, butanol and a mixture thereof, to the bio-sludge or the biochar.

Bio-derived solid waste sludge may be sourced from wastewater treatment plant, and typically contains about 75-85% moisture. In an embodiment, the content of moisture used in the process is about 10% to about 90%, about 50 to about 85%, or from about 5% to about 50%.

In certain embodiments, anhydrous sludge or a sludge having residual content of less than 50% moisture may be used in the process.

Biochar is produced using bio-sludge as feedstock by performing pyrolysis in a furnace. Pyrolysis can be performed at different temperatures ranging from about 300 to 800° C. Typically, it is carried out at about 300° C., 500° C. or 800° C.

The amount of solvent can range from about 1 to about 10 times of the quantity of the bio sludge or biochar. The preparation of suspension is carried out at a temperature of about 10° C. to about 50° C. for about 15 min to about 10 hours.

Step c):

The step of mixing the suspensions obtained in step a), and step b) can be carried out at a temperature of about 10° C. to about 50° C. for about 1 hour to 20 hours, or from about 1 hour to about 15 hours.

In an embodiment, the process involves mixing a suspension (sol) containing $TiO_2$ particles in a hydrated form, obtained in step iii) of step a), with the suspension of step b). This is particularly suitable, when bio-sludge is employed in step b). This represents the sol-gel method.

In another embodiment, the process comprises mixing the suspension of step b) with the $TiO_2$ obtained from step iv) of step a), either in dry form or as a suspension in an alcohol. This is particularly suitable when biochar is employed in step b). This represents self-assembly approach.

Step d):

The drying is carried at high temperatures of about 500° C. for about 2 h to about 10 h. Any drying technique, such as normal over drying, micro-oven drying, and the like, may be employed.

In a specific embodiment, the dried product is calcined at a temperature of about 500° C. to about 800° C. for about 2 to about 6 hours. In a further specific embodiment, it is calcined at a temperature of about 500° C. for about 2 hours.

In certain embodiments of the method, the loading of bio-sludge or biochar on $TiO_2$ ranges from about 1% to about 10 wt %, from about 1% to about 5%, or about 3% when compared to the total weight of the composite.

In a specific embodiment, the present disclosure provides a method for producing a nanocomposite of biosludge/$TiO_2$. The method comprises the steps of:

a) preparing a suspension of $TiO_2$ precursor in an alcoholic solvent;
b) adding an acid to hydrolyze the precursor;
c) preparing a suspension of bio-sludge in an alcoholic solvent;
d) mixing the suspensions obtained in step b), and step c) to obtain a suspension of the $TiO_2$ precursor and bio-sludge; and
e) drying and calcining the suspension obtained in step d).

In another specific embodiment, the present disclosure provides a method for producing a nanocomposite of biochar/$TiO_2$. The process comprises the steps of:

a) preparing a suspension of $TiO_2$ particles in an alcoholic solvent;
b) preparing a suspension of biochar in an alcoholic solvent;
c) mixing the suspensions obtained in step a), and step b) to obtain a suspension of the $TiO_2$ nanoparticles and biochar; and
d) drying and/or calcining the suspension obtained in step c).

For the method for producing a nanocomposite of bio-sludge/$TiO_2$ or biochar/$TiO_2$, the process conditions are similar to those defined for the embodiment directed to the method for producing bio-sludge or a biochar/$TiO_2$ nanocomposite material described above.

In yet another aspect, the present disclosure provides a bio-sludge or a biochar/$TiO_2$ nanocomposite material prepared by the method of any of the preceding embodiments.

In an embodiment, the nanocomposite material is a 2D/0D bio-sludge or bichar/$TiO_2$ nanocomposite material. The nanocomposite material has a structure where the biochar acts as a two-dimensional (2D) support or substrate, while the $TiO_2$ nanoparticles serve as zero dimensional (0D) active sites or components dispersed on or within the bio-sludge or biochar matrix. The nanocomposite has a hierarchical nanotexture with one or more layers. The bio-sludge/biochar loading in the composite is about 1 wt % to about 10 wt %, from about 1 wt % to 5 wt %, or about 3 wt % when compared to the total weight of the composite.

The nanocomposite provided by the present disclosure is useful for photocatalytic $CO_2$ reduction. Therefore, the present disclosure further provides a process for $CO_2$ reduction.

In an aspect, the present invention provides a process for photocatalytic reduction of $CO_2$ using the bio-sludge or a biochar/$TiO_2$ nanocomposite material of the present disclosure. The process comprises contacting a feed comprising $CO_2$ and at least one sacrificial compound with a composite photocatalyst provided in any of the preceding embodiments, in a photocatalytic system; and irradiating the photocatalyst with at least one irradiation source.

The sacrificial compound comprises water, $H_2$, methanol, or their mixtures. In a specific embodiment, the sacrificial compound comprises water, $H_2$, $H_2$-water mixture, or methanol-water mixture, methane, ethanol, acetic acid, propanol, glycerol, TEOA, or a mixture thereof.

The mechanism of photocatalytic $CO_2$ reduction with $H_2O$/methanol to produce CO and $CH_4$ over BS/BSC loaded $TiO_2$ composite under solar irradiation involves production of holes and electrons over the surface of $TiO_2$ by light irradiation. The electrons and holes produced over the $TiO_2$ surface are trapped by cocatalysts, which were beneficial for promoting $TiO_2$ photocatalytic efficiency. The production of charges over $TiO_2$ and their separation with metal elements and utilization for oxidation and reduction reactions are represented in Eqs. (1) to (6).

$$TiO_2 + h\nu \xrightarrow{\text{light}} e^-_{CB} + h^+_{VB} \quad (1)$$

$$M + e^-_{CB} \longrightarrow M(e^-_{CB}) \quad (2)$$

$$2H_2O + 4h^- \longrightarrow 4H^+ + O_2 \quad (3)$$

$$CO_2 + 2H^+ + 2e^- \longrightarrow CO + 2H_2O \quad (4)$$

$$CO_2 + 8H^+ + 8e^- \longrightarrow CH_4 + 2H_2O \quad (5)$$

$$CH_3OH + H_2O \longrightarrow CO_2 + 6H^+ + 6e^- \quad (6)$$

Figure 4:
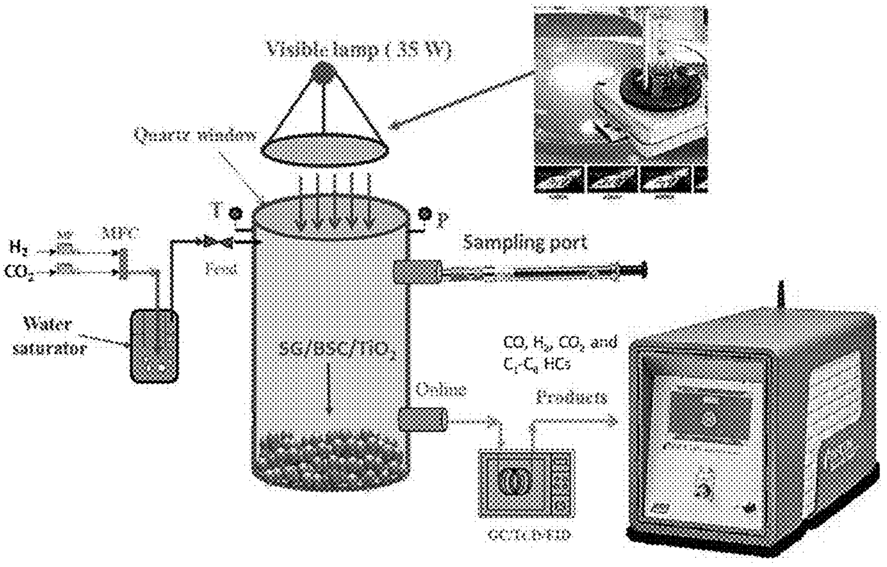
FIG. 4 shows Experimental set-up for photocatalytic $CO_2$ reduction.

In a specific embodiment the process for $CO_2$ reduction is carried at a temperature of about 20° C. to 100° C. In some embodiments, the process is carried out at room temperature and atmospheric pressure. In some embodiments the process for $CO_2$ reduction is carried for a time period of about 1 to 20 hours Typically, the photocatalysis is conducted in a cell-type fixed bed photoreactor system made of stainless steel with inlet and outlet connections, a glass window for passing light irradiations and a heater with a control to adjust the temperature. A 35W Xenon Lamp (CAR HID light) is used as the main light source, producing light with an intensity of 20 mW/cm$^2$. This lamp allows light to enter the reactor chamber since it is positioned above a quartz glass window. A water saturator is incorporated into the reactor system to transport $CO_2$ and either moisture or a combination of methanol and water. An illustrative and typical schematic representation of the experimental set-up for photocatalytic $CO_2$ reduction is shown in FIG. 4.

The reactor can be employed for feed mixtures such as $CO_2$ with water, $CO_2$ with $H_2$ and $CO_2$ with methanol/water. The photocatalyst typically in a weight of about 150 mg is equally dispersed across the reactor's bottom surface before starting the photocatalytic $CO_2$ reduction. The catalyst surface is crossed by the feed mixture as it enters from the top and left at the bottom. The primary exposed region is the bottom surface of the reactor chamber, which is where the catalyst, reactants, and light source interact.

In a specific embodiment, the reduction is typically conducted at a continuous flow of $CO_2$ either combined with $H_2O$ or a mixture of $H_2O$/methanol of about 15 mL/min. In the case of $CO_2/H_2$ experiments, a $CO_2/H_2$ mixture of ratio 1:1 can be used. The reduction can be conducted at atmospheric pressure and temperature can be varied from room temperature to about 100° C. depending on the type of experiment. The products are analyzed using INFICON GC (μGC), which is attached to two TCD detectors.

In a specific embodiment, the photocatalytic system comprises a main reactor chamber, one or more cooling fans integrated with an irradiation light source, one or more mass flow controllers (MFC), and an online products analysis system.

According to the present disclosure, any light or irradiation source emitting wavelengths absorbable by the photocatalyst can be utilized for activation. These sources may include natural sources like sunlight or artificial sources such as lasers, Hg lamps, incandescent lamps, fluorescent tubes, plasma, or Light-Emitting Diodes (LEDs). In some embodiments, the irradiation source is a Hg lamp. In some embodiments, a 35W Xenon Lamp (CAR HID light) is used as the main light source, producing light with an intensity of 20 $mW/cm^2$ is used in the process.

In a specific embodiment, the irradiation source is positioned external to the reactor, and their interaction occurs through an optical interface. This interface, which facilitates the diffusion of photons absorbable by the photocatalyst into the reactor, can be constructed from materials such as quartz, glass, or any other suitable material. In a further specific embodiment, the optical interface is a quartz glass window, and the irradiation source located above the optical interface.

In a further specific embodiment, a water saturator is integrated into the reactor system to facilitate the transportation of moisture, or water-containing mixtures such as $H_2$-water mixture, methanol-water mixture, and the like along with $CO_2$. This integration ensures a controlled and efficient delivery of these compounds into the reactor environment. The water saturator operates by saturating the carrier gas, typically $CO_2$, with water vapor. By passing the $CO_2$ through the water saturator, moisture or the water-containing mixture becomes effectively carried along with the $CO_2$ stream into the reactor. This ensures a consistent and controlled supply of the desired compounds, essential for the successful execution of various photocatalytic processes within the reactor system.

In a further specific embodiment, the feed enters the reactor at the top and flows over the catalyst surface before exiting at the bottom. The bottom surface of the reactor chamber, where a uniformly distributed powder photocatalyst is present, serves as the primary area for interaction among the catalyst, reactants, and light source. Before commencing the experiments, a feed or feed mixture (e.g., $CO_2$ and $H_2O$) is continuously passed through the reactor for a predetermined time to saturate the catalyst surface.

In a specific embodiment, the process selectively or majorly produces CO when $CO_2$ reduction is carried out with water. In some embodiments, when $CO_2$ is reduced with a methanol-water mixture, both CO and $CH_4$ are produced in significant amounts.

When methanol is used as a hole scavenger, it enhances the conversion of $CO_2$ into CO over the nanocomposite of the present disclosure. Methanol-water mixture exhibits superior performance compared to water and $H_2$, significantly increasing CO yield. The process involves increased proton and electron production during photocatalysis, facilitating $CO_2$ reduction to form CO.

The process yields $CH_4$ during photocatalytic $CO_2$ reduction with $H_2O$ and $H_2$. However, higher yields are achieved when employing methanol as the sacrificial reagent. Notably, the addition of a methanol-water mixture significantly enhances $CH_4$ generation compared to using water or $H_2$ alone.

The process for $CO_2$ reduction with the composite of the present disclosure produces CO, $CH_4$, and $H_2$ during the methanol-driven reforming. This demonstrates the efficacy of the process in promoting multiple reaction pathways and facilitating the formation of diverse carbon-based products.

The nanocomposites of the present invention result in efficient hydrogen conversion and $CO_2$ reduction under solar energy. The nanocomposites find application in the field of solar panels to enhance electricity production, purification of water at low cost, solar cells, fuel cells, and other fields of nanotechnology.

The present disclosure is further described with reference to the following examples, which are only illustrative in nature and should not be construed to limit the scope of the present disclosure in any manner.

EXAMPLES

Analytical Methods:

The crystal structure of the material was analyzed using powder X-ray diffraction (XRD) on a Bruker Advance D8 diffractometer with a Cu Kα radiation of λ=0.154 nm.

The morphologies of the pure and the composite materials were analyzed using Hitachi SU8020 SEM (Scanning Electron Microscopy) and JEOL JEM-ARM 200F TEM (Transmission Electron Microscopy).

The EDS (Energy Dispersive X-ray Spectroscopy, OXFORD) was used to determine the distribution of elements and their composition.

The valence band (VB) spectra and surface chemical compositions were evaluated on an X-ray photoelectron spectroscopy (XPS, Axis Ultra DLD).

The Fourier Transform Infrared Spectroscopy (FTIR) analysis was conducted to determine functional groups.

Using the UV-3600 Plus Spectrometer, the band gap energy and light absorption were estimated. At a wavelength of 532 nm, the HORIBA spectrometer was used to perform the Raman analysis. Raman-PL was used to determine charge carrier separation on a HORIBA Scientific Spectrometer (laser 325 nm and 532 nm).

EXAMPLES

Example 1: Preparation of Bio-Sludge (BS) and Bio-Sludge Derived Char (BSC)

Bio-derived solid waste sludge collected from wastewater treatment plant containing 75-85% moisture was placed in an oven to remove moisture. The sludge was then dried for 24 hours at 100° C. (until a moisture content of 2 to 5%) to yield Bio-sludge (BS).

Using bio-sludge (BS) as the feedstock, a pyrolysis technique was performed to prepare Bio-sludge derived biochar (BSC). Specifically, 5 to 10 g of the bio-sludge was heated in a furnace at different temperatures ranging from 300 to 800° C. for one hour and was named BSC-300, BSC-500 and BSC-800. The Schematic for the synthesis of BS and BSC at different temperatures has been demonstrated in FIG. 1.

Figure 2:
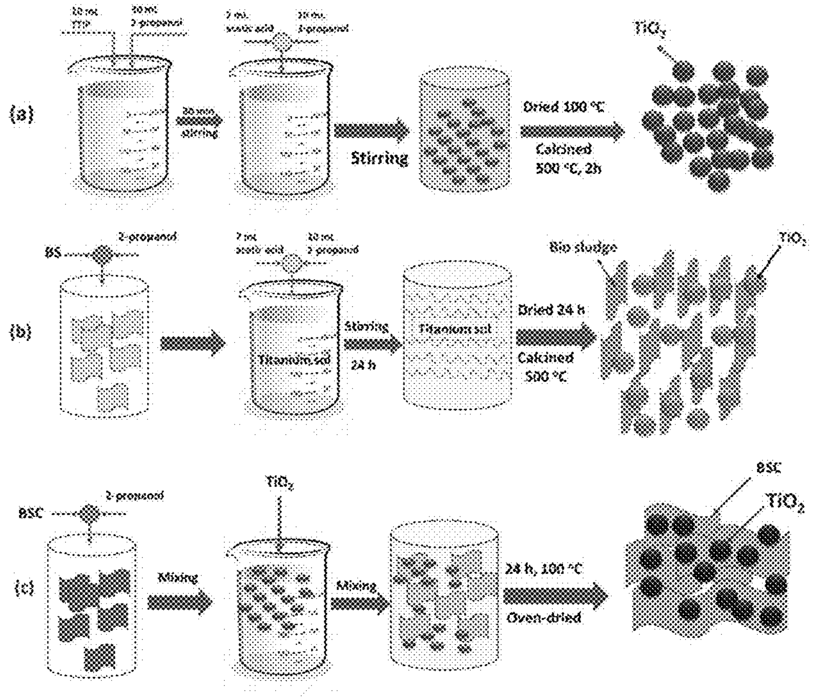
FIG. 2 shows schematic illustration for the (a) Synthesis of $TiO_2$, (b) Sol-gel synthesis of BSC/$TiO_2$, (c) BSC/$TiO_2$ synthesis through self-assembly.
Figure 3:
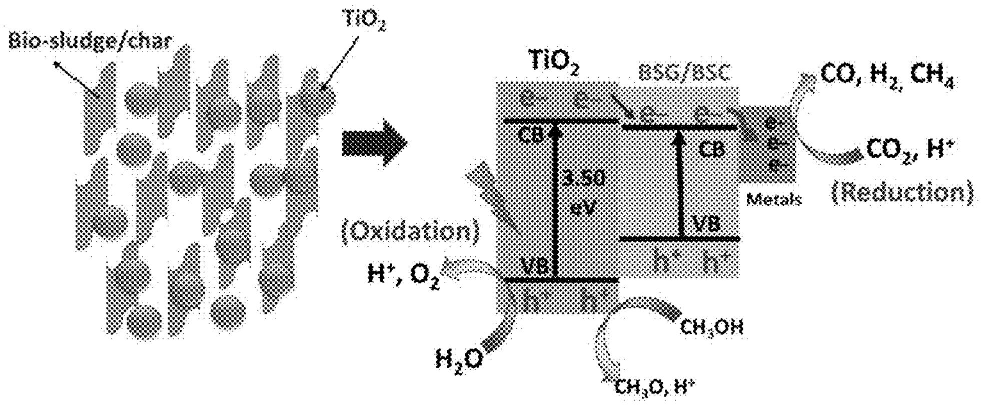
FIG. 3 depicts the schematic mechanism for photocatalytic $CO_2$ reduction with methanol/water mixture over BS/BSC supported $TiO_2$ composite.

Example 2: Synthesis of $TiO_2$ Using Sol-Gel Method 5-10 mL of titanium tetra-isopropoxide (TTIP) was dissolved in 2-propanol (10 to 40 ml. Titanium sol was produced by hydrolyzing TTIP in acetic acid (1M). The suspension was then stirred for the next 12 hours and finally dried at 100° C. in an oven overnight. Following this, the resultant product was ground into a fine powder and heated to 500° C. for two hours to produce pure $TiO_2$. A schematic depiction of the synthesis of $TiO_2$ is presented in (a) of FIG. 2.

Example 3

Synthesis of BSC/$TiO_2$ Using Sol-Gel Method 5-10 mL of titanium tetra-isopropoxide (TTIP) was dissolved in 2-propanol 10 to 40 ml. Titanium sol was produced by hydrolyzing TTIP in acetic acid (1M)-5 to 10 ml. After four hours of stirring, a precise quantity of BS (3-10%) dispersed in 2-propanol was added to the titanium solution. The suspension that was left over was then stirred for the next 12 hours and finally dried at 100° C. in an oven overnight. Following this, the resultant product was ground into a fine powder and heated to 500° C. for two hours to yield BSC-500/$TiO_2$ composite. A schematic depiction of the synthesis of BSC/$TiO_2$ composites is presented in (b) of FIG. 2.

Example 4: Synthesis of BSC/$TiO_2$ Using Self-Assembly Approach 50-100 mg of $TiO_2$ was dispersed in 20 mL of methanol and stirred well for 2 hours. In parallel, to obtain good surface interaction, a particular amount of BSC dispersed in 20 mL methanol was added to the aforesaid suspension and agitated for an additional two hours. The suspension was then oven-dried at 100° C. to get the final product and was given the name BSC/$TiO_2$ composite. The schematic illustration is shown in (c) of FIG. 2.

Example 6: Photocatalytic $CO_2$ Reduction

Example 6(a) Photocatalytic $CO_2$ Reduction Using Methanol/Water Mixture

A series of blank experiments were run to investigate the existence of organic molecules in the produced photocatalysts and their effect on the potential production of CO, and $CH_4$. Specifically, three scenarios were tested.

(1) a feed mixture and light source with no photocatalyst;

(2) a photocatalyst and feed mixture with no light source; and (3) a feed mixture and light source with no photocatalyst.

In all of these trials, no products such as CO, and $CH_4$ were generated, suggesting that the photocatalyst is clean.

The performance of all the photocatalysts were conducted under visible light irradiation in a continuous flow photoreactor system. To do this, 150 mg of the catalyst was added to the reactor, and tests were run with visible light of intensity 20 mW/cm$^2$. The compressed $CO_2$ gas is regulated at a flow rate of 15 mL/min through a water saturator to carry moisture before entering the reactor. For the case of methanol/water mixture, 10% methanol was added to water saturator. In the case of photocatalytic $CO_2$ reduction with $H_2$, a feed mixture of 80% $H_2$ and 20% $CO_2$ with a total flow rate of 15 mL/min was passed through the photoreactor.

Figure 5A:
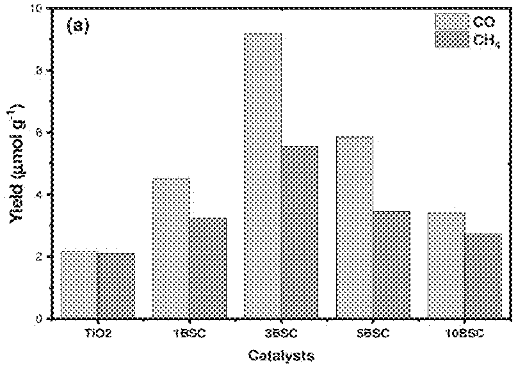
FIG. 5A shows photocatalytic $CO_2$ reduction with $H_2O$ to produce CO and $CH_4$ over $TiO_2$ and BSC loaded $TiO_2$ samples in a continuous flow photoreactor.

Results and Discussion:

FIG. 5A shows the results of CO and $CH_4$ production during photocatalytic $CO_2$ reaction with water over $TiO_2$ and various BSC loading (1 to 10%) with $TiO_2$. The principal products produced were CO and $CH_4$, while their production yield was different. The results are tabulated below:

| Catalyst | Yield of CO (in μmol $g^{-1}$) | Yield of $CH_4$ (in μmol $g^{-1}$) |
|---|---|---|
| $TiO_2$ | 2.17 | 2.11 |
| 3% BS/$TiO_2$ | 4.51 | 4.24 |
| 3% BSC/$TiO_2$ | 9.175 | 5.56 |
| 5% BSC/TiO2 | 5.86 | 3.36 |
| 10% BSC/TiO2 | 3.41 | 2.74 |

With BSC loading to $TiO_2$ photoactivity was increased. Using optimized 3% BSC/$TiO_2$ composite, the highest CO production as the main product was 9.175 μmol $g^{-1}$ after 2 hours of irradiation time. This amount of CO production was 4.23 folds higher than using pristine $TiO_2$. Similarly, the highest $CH_4$ production of 5.56 μmol $g^{-1}$ was obtained with optimized 3% BSC/$TiO_2$ composite. This amount of $CH_4$ production was 2.63 folds higher than using pristine $TiO_2$. This increase in photocatalytic activity was due to efficient charge carrier separation within the BSC/$TiO_2$ composite. This illustrates how the conductive properties of biochar encourage the use of metallic elements in oxidation and reduction reactions. Despite being a co-catalyst because of its high electrical conductivity, metallic elements (M) were beneficial for increasing the photocatalytic activity of biochar during the $CO_2$ reduction process. On the other hand, when the BSC loading was increased to 5 and 10 wt. %, the photocatalytic efficiency for CO and $CH_4$ production was decreased. Increased biochar content unquestionably lowers activity because particle agglomeration diminishes the active regions on the $TiO_2$ surface. The formation of photo-generated charge carrier recombination centres is also connected to the decline in activity.

Figure 5B:
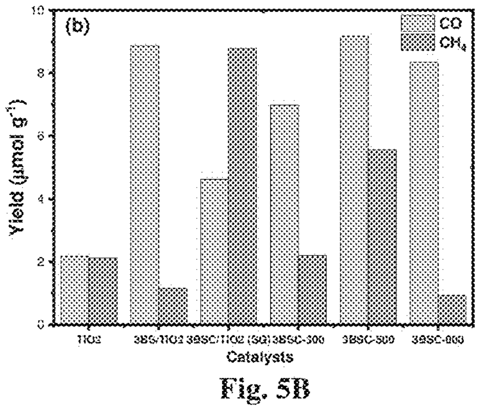
FIG. 5B shows photocatalytic $CO_2$ reduction with $H_2O$ to produce CO and $CH_4$ over various photocatalysts in a continuous flow photoreactor.

FIG. 5B shows the results of CO and $CH_4$ production during photocatalytic $CO_2$ reaction with water over $TiO_2$, 3% BS/$TiO_2$ composite, 3% BSC/$TiO_2$ (SG), 3% BSC/$TiO_2$-300, 3% BSC/$TiO_2$-500, and 3% BSC/$TiO_2$-800. The results are tabulated below:

| Catalyst | Yield of CO (in μmol $g^{-1}$) | Yield of $CH_4$ (in μmol $g^{-1}$) |
|---|---|---|
| $TiO_2$ | 2.17 | 2.11 |
| 3% BS/$TiO_2$ | 8.87 | 1.16 |
| 3% BS/$TiO_2$ sol-gel (SG) | 4.63 | 8.79 |
| 3% BSC/$TiO_2$-300 | 6.98 | 2.21 |
| 3% BSC/$TiO_2$-500 | 9.18 | 5.56 |
| 3% BSC/$TiO_2$-800 | 8.35 | -.93 |

When 3% BS/$TiO_2$ composite was tested, CO and $CH_4$ yield rates of 8.87 and 1.16 μmol $g^{-1}$ were produced. This shows that bio-sludge is also an efficient cocatalyst to enhance $TiO_2$ photocatalytic efficiency. This was due to the presence of sludge elements, which prevent charge recombination, and increase their lifetime. Comparing the performance of BS/$TiO_2$ and BSC/$TiO_2$, the photocatalytic efficiency of biochar (BSC) loaded with $TiO_2$ was 1.03 and 4.79 folds more for CO and $CH_4$ production. This shows that bio-sludge converted to biochar is more efficient in increasing $TiO_2$ photocatalytic efficiency. The higher $CH_4$ production with BSC/$TiO_2$ further confirms more production of electrons and protons during the photocatalysis process.

Furthermore, biochar synthesized at 500° C. was best to maximize the photocatalytic efficiency of $TiO_2$. Using 3% BSC-500/$TiO_2$, CO production rates were 1.098 and 1.31 folds and $CH_4$ production rates of 5.97 and 2.525 folds more than using BSC-800° C. and BC-300° C., samples, respectively. This was due to the complete conversion of biosludge to biochar at 500° C. with the stable conditions of metal oxides compared to using very high (800° C.) or very low (300° C.) temperatures. More interestingly, when the samples were prepared using the sol-gel process (SG), in which bio-sludge and $TiO_2$ were heated together to produce % $BSC/TiO_2$ (SG), the production of $CH_4$ was increased to 8.79 μmol $g^{-1}$, which was highest compared to all other samples. This increase in photocatalytic efficiency can be described based on good interface interaction, resulting in significantly more production and separation of electrons. For $CH_4$ production, 8 electrons are required, compared to using only 2 electrons for CO formation, which were effectively obtained when the samples were synthesized using the sol-gel process.

Figure 5C:
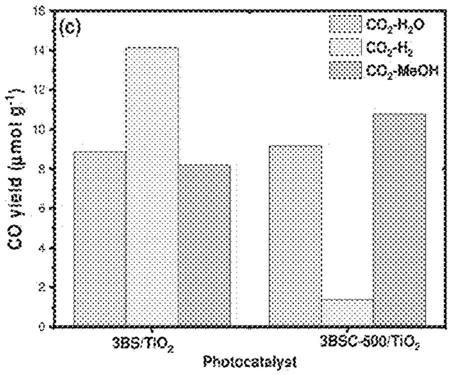
FIG. 5C shows the performance of different materials such as 3% BS/$TiO_2$, 3% BS/$TiO_2$ (SG) and BSC-loaded $TiO_2$ synthesized at different calcination temperatures (d) Effect of sacrificial reagents on the performance of BS/$TiO_2$ and BSC/$TiO_2$ composites for the production of CO during the $CO_2$ reduction process.

Example 6(b) Photocatalytic $CO_2$ Reduction with Different Reaction Systems (H2O, H2, and CH3OH) Over $3BSC/TiO_2$, and $3BSC/TiO_2$ Results and Discussions:

FIG. 5C shows the production of CO during $CO_2$ reduction with different reaction systems. The highest CO production of 14.15 μmol $g^{-1}$ was obtained during $CO_2$ reduction with $H_2$ over $3BS/TiO_2$ composite, which is 1.59 and 1.72 folds more than using water and methanol/water mixtures, respectively. On the other hand, using $3BSC/TiO_2$ composite, the highest CO production of 10.77 μmol $g^{-1}$ was obtained with methanol, which was 1.17 and 7.82 folds more than using $CO_2/H_2O$ and $CO_2/H_2$ feed mixtures. These results show that the performance of the catalyst is entirely dependent on the type of reducing agents employed. In general, both the materials $BS/TiO_2$ and $BSC/TiO_2$ were beneficial to maximize the $TiO_2$ photocatalytic efficiency, whereas, their results were different.

Figure 5D:
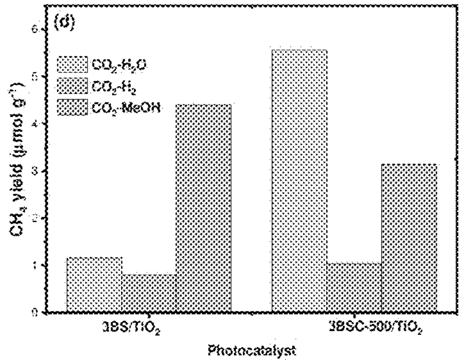
FIG. 5D shows the production of $CH_4$ during $CO_2$ reduction with different reaction systems.

FIG. 5D shows the production of $CH_4$ during $CO_2$ reduction with different reaction systems. The highest $CH_4$ production of 4.4 μmol $g^{-1}$ was obtained during $CO_2$ reduction with methanol over $3BS/TiO_2$ composite, which is 3.39 and 5.5 folds more than using $CO_2$/water and $CO_2/H_2$ mixtures, respectively. On the other hand, using $3BSC/TiO_2$ composite, the highest $CH_4$ production of 5.56 μmol $g^{-1}$ was obtained with a $CO_2$/water mixture, which was 1.76 and 5.35 folds more than using $CO_2$/methanol and $CO_2/H_2$ feed mixtures. These results show that the performance of the catalyst is entirely dependent on the type of reducing agents employed. The presence of either hydrogen or methanol was not beneficial in enhancing the production of $CH_4$, however, they enabled to maximize of the production of CO.

Figure 6:
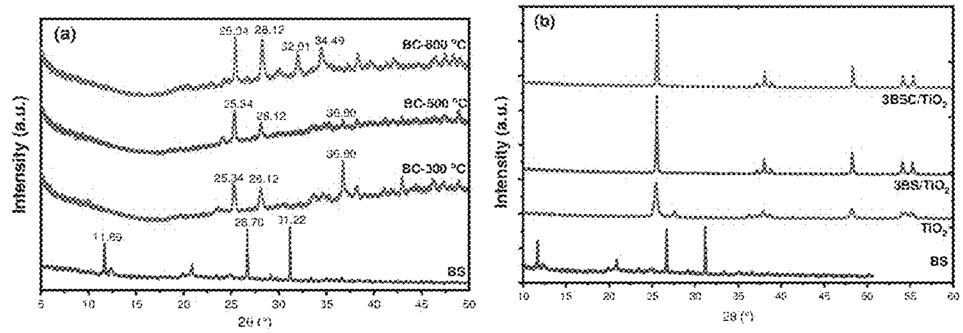
FIG. 6 depicts (a) XRD analysis of bio-sludge and bio-sludge derived biochar at temperatures of 300, 500° C. and 800° C., (b) XRD of $TiO_2$ and BS/$TiO_2$ and BSC/$TiO_2$ samples.

Characterization of Nanocomposite Material Comprising 2D/0D Bio-Sludge or $Biochar/TiO_2$:

XRD Analysis of Samples:

FIG. 6 in (a) shows XRD analysis of bio-sludge (BS) and bioderived char (BC). The prominent peaks for BS appear at 2θ of 11.69°, 26.70° and 31.22° and these can be linked to organic complex, $SiO_2$, and $Fe_3O_4$, respectively. On the other hand, bio-sludge often contains significant amorphous material (organic matter, amorphous silica, etc.) that does not produce distinct XRD peaks.

When bio-sludge is heated to 300, 500 and 800° C., the 20 peak positions change, whereas, some peaks disappear and new peaks are produced. The peak 2θ of 11.69° disappears due to heating at higher temperatures and decomposition of organic-based materials. However, three main peaks appear when the sample is heated at 300° C. with 2θ values of 25.34°, 28.12° and 36.80°. The peak at 2θ values of 25.34° can be ascribed to graphitic carbon, whereas, the other two peaks at 2θ of 28.12° and 36.80° can be ascribed to silicon dioxide and silicon carbide, respectively.

When the temperature is increased to 500° C., the peak at 36.80° disappears. All the 2θ peaks for BC at 500° C. are linked mainly to silicon carbide. Furthermore, when the temperature is further increased to 800° C., more obvious peaks appear, which are possibly due to decomposition of organics and the formation of oxides which are present in the bio-sludge.

FIG. 6 in (b) shows XRD patterns of $TiO_2$, $BS/TiO_2$ and $BC/TiO_2$ samples. The anatase phase of $TiO_2$ is represented by the diffraction peaks in the XRD patterns of pure $TiO_2$ that belong to the lattice plans of (101), (004), (200), (220), and (215). Nevertheless, a different lattice plan at (110) verifies the existence of $TiO_2$'s rutile phase. All these findings confirm the successful synthesis of pure and composite materials useful for various photocatalytic applications. 2θ peaks related to BS and BSC were not appeared due to very small amount of loading and they were below the detection limit of the machine.

Raman Analysis:

The Raman analysis of bio sludge (BS), bio-sludge char (BSC), $TiO_2$ and BSC coupled $TiO_2$ were investigated to identify the molecular fingerprints and interactions among the composite materials through determining their vibrational modes.

Figure 7:
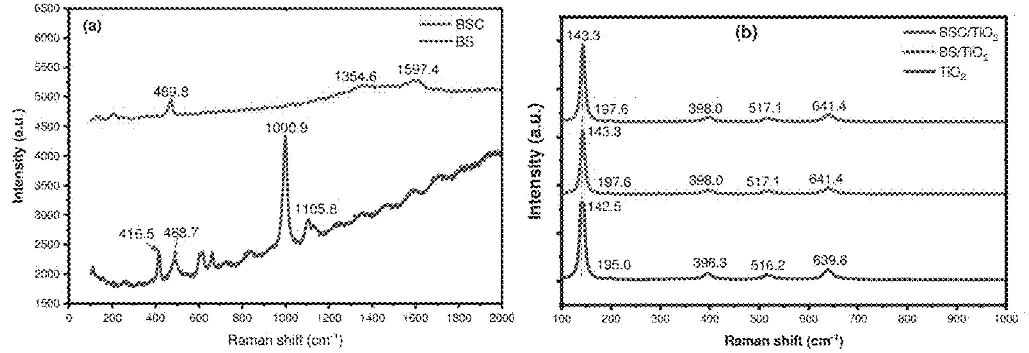
FIG. 7 depicts (a) Raman analysis of BS and BSC samples, (b) Raman analysis of $TiO_2$, BS/$TiO_2$ and BSC/$TiO_2$ samples.

FIG. 7 in (a) shows the Raman shift of BS and BSC samples. For the pure BS, the vibrational modes appear at 416.5, 488.7, 1000.9 and 1105.8 $cm^{-1}$, however, these modes disappear when the sludge is heated to 800° C. For the BSC, new Raman modes appear at 1354.6 and 1597.4 $cm^{-1}$, which can be ascribed to the D band and G band. While the G band is associated with the vibrations of sp2-hybridized carbon atoms in graphitic carbon layers, the D band is associated with disordered carbon structures. A significant degree of carbon organization is suggested by the distinct and strong peaks. The biochar spectra have a strong peak at 469.8 $cm^{-1}$, which correlates to the $SiO_2$ vibrational mode $SiO_2$.

FIG. 7 in (b) shows Raman modes of $TiO_2$, $BS/TiO_2$ and $BSC/TiO_2$ samples. For the pure $TiO_2$, Raman modes appear at 142.5, 195.0, 396.3, 516.2, 639.6 $cm^{-1}$, which can be ascribed to the anatase phase of $TiO_2$. When BS and BSC were added to $TiO_2$, there are shifts in modes, which confirm a good interaction among both materials.

Figure 8:
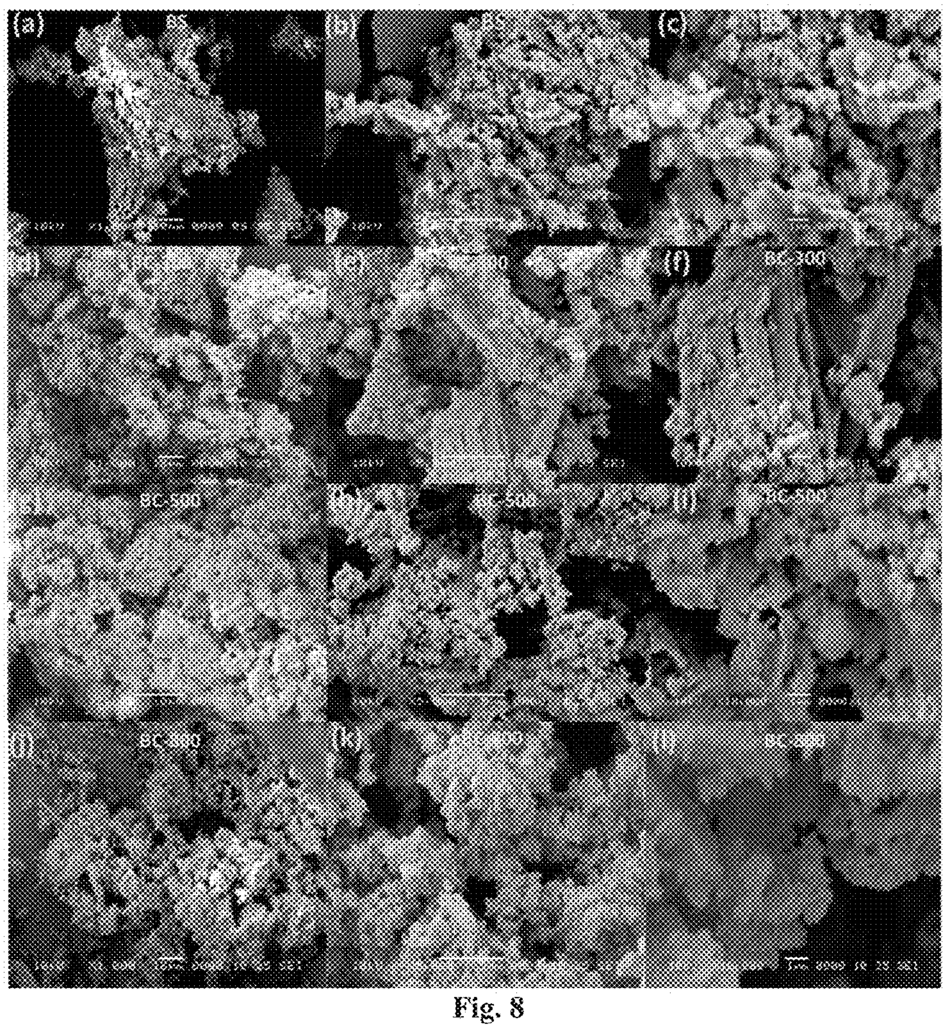
FIG. 8 depicts SEM analysis of (a-c) bio-sludge (BS), (d-f) bio-sludge char prepared at 300° C. (BSC-300° C.), (g-i) bio-sludge char prepared at 500° C. (BSC-500° C.), (j-l) bio-sludge char prepared at 800° C. (BSC-800° C.).

Morphology:

FIG. 8 shows the morphology of bio-sludge, and the bio-sludge char. These are synthesized at calcination temperatures 300° C. (BSC-300° C.), 500° C. (BSC-500° C.) and 800° C. (BSC-800° C.). The chaotic and incompact platy structure of bio-sludge, which is made up of aggregates of flat sheets with walls and different thicknesses, is shown in FIG. 8 in (a-c). This shows that bio-sludge is made of sheet-like structure due to the presence of organic materials. FIG. 8 in (d-f) shows the morphology of bio-sludge char produced by heating at 300° C. Each produced biochar's porous framework was visible in the SEM micrographs, displaying a variety of mesopore and micropore morphologies. The biochar morphology is similar to bio-sludge, in which a sheet-like structure with a porous structure can be observed. When the sample is further heated to 500° C. and 800° C., there is no significant difference in morphologies. FIG. 8 in (g-i) shows the morphology of BSC-500° C., in which more porous and obvious sheets can be observed. Similarly, as shown in FIG. 8 in (j-l), a obvious porous structure with 2D layered sheets can be obtained, which are due to decomposing organic materials present in the biosludge. All these results show successful synthesis of the biochar which is beneficial to maximize the $TiO_2$ photocatalytic efficiency.

Figure 9:
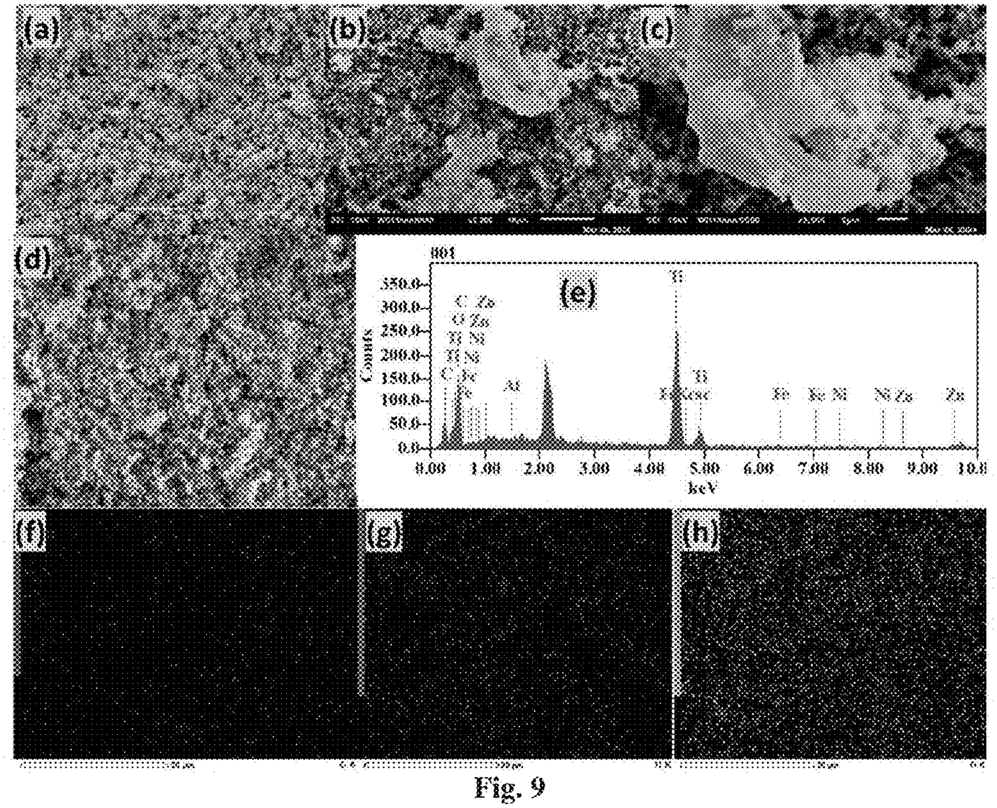
FIG. 9 depicts SEM analysis of BSC/$TiO_2$ samples: (a) SEM of $TiO_2$, (b-c) SEM of BSC/$TiO_2$, (d-h) EDS mapping analysis of BSC/$TiO_2$, (e) EDX spectra for the identification of elements.

FIG. 9 in (a) shows the morphology of $TiO_2$, in which $TiO_2$ nanoparticles of uniform size can be observed. Furthermore, when BSC-800° C. is added to $TiO_2$, a good interface interaction with the layered structure of BSC can be obtained as shown in FIG. 9 in (b-c). These results show a successful synthesis of the BSC/$TiO_2$ composite.

The EDX mapping analysis is further conducted to see the distribution of elements and the results are shown in FIG. 9 in (d). It can be observed that the BSC/$TiO_2$ is entirely covered with several elements such as C, O and Ti. The presence of elements is further confirmed by the EDX spectra as shown in FIG. 9 in (e), in which several peaks related to Zn, Ni, Ti, O, and Fe are obtained. Most of these elements are present due to bio-sludge. The colour images in FIG. 9 in (f-h) further confirm the uniform distribution of BSC/$TiO_2$ elements such as C, O and Ti.

Figure 10:
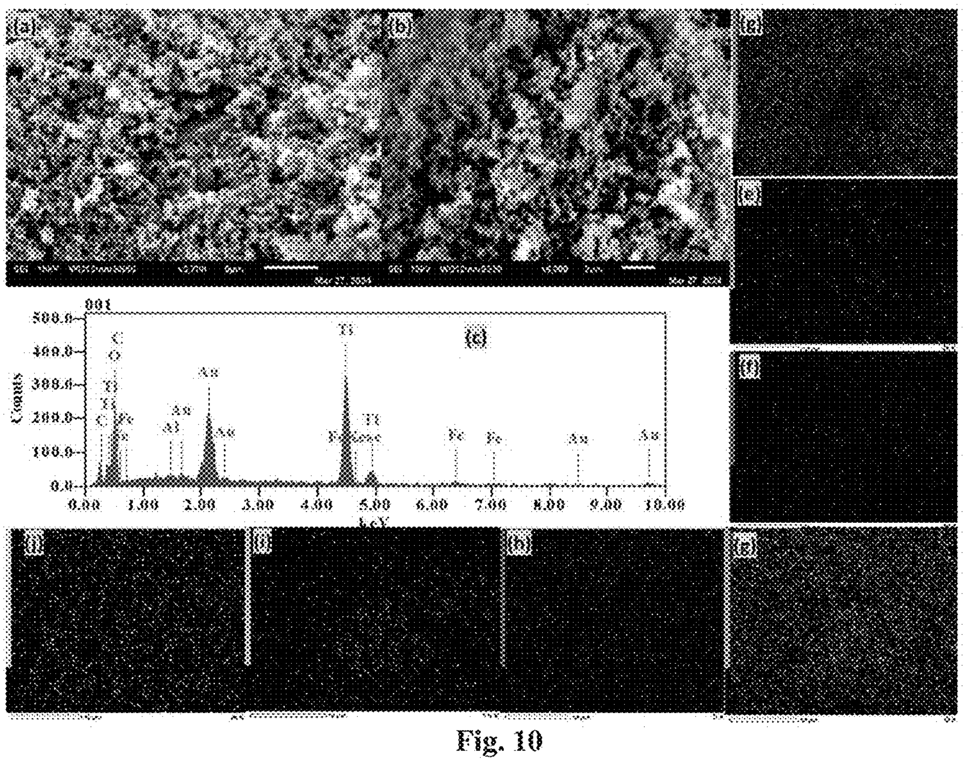
FIG. 10 depicts SEM analysis of BS/$TiO_2$: (a-b) SEM of BS/$TiO_2$ composite, (c) EDX spectra of BS/$TiO_2$, (d-j), EDS mapping analysis of BS/$TiO_2$.

SEM and EDS Mapping Analysis:

FIG. 10 shows SEM and EDS mapping analysis of the BS/$TiO_2$ composite. The surface morphology of BS/$TiO_2$ shows that the $TiO_2$ particles are evenly distributed throughout the bio-sludge and do not aggregate, as shown in FIG. 8 in (a-b) [23]. The interaction between the elements within the BC/$TiO_2$ composite is further investigated using EDX mapping analysis. FIG. 10 in (c) shows the EDX spectra of BS/$TiO_2$, which confirms the presence of sludge elements. The main elements identified were Ti, Zn, O, Ni, C, Fe and Al, as shown in FIG. 10 in (d-f), respectively. All these images with uniform colour distribution confirm good interaction between the sludge and $TiO_2$ elements.

Figure 11:
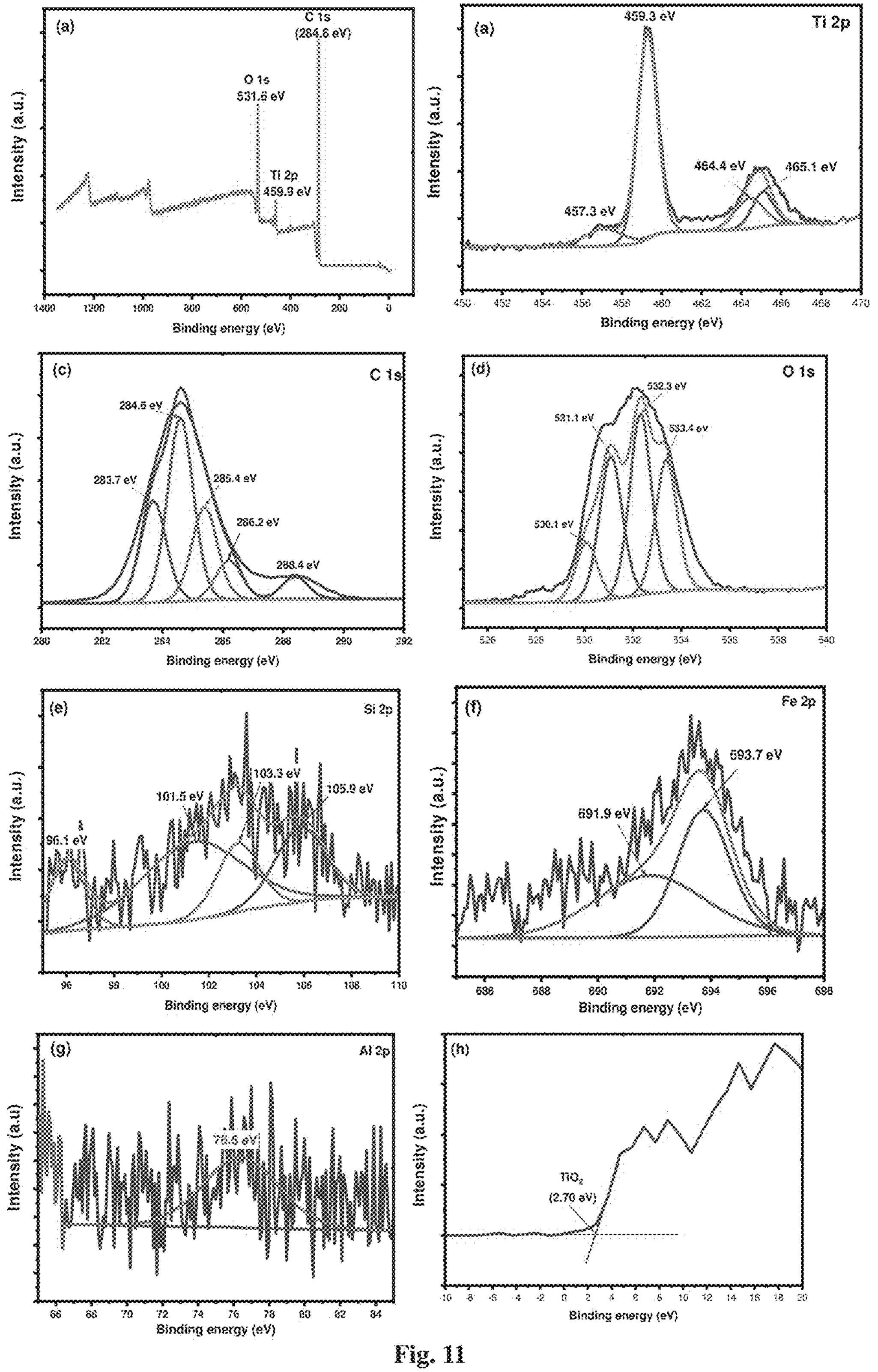
FIG. 11 depicts XPS analysis of BS/$TiO_2$ composite: (a) wide spectra, (b) Ti 2p, (c) C 1s, (d) O 1s, (e) Si 2p, (f) Fe 2p, (g) Al 2p, (h) wide spectra to calculate valance band position.

X-Ray Photoelectron Spectroscopy (XPS) Analysis:

X-ray photoelectron spectroscopy (XPS) analysis of the BS/$TiO_2$ composite is further conducted to get information about the composition and elemental states and the results are presented in FIG. 11. FIG. 11 in (a) shows wide spectra confirming the existence of the main elements which include C, Ti and O. FIG. 11 in (b) shows high-resolution XPS spectra for Ti 2p with binding energies of 459.3 (Ti $2p_{3/2}$) and 463.1 eV, indicating the presence of titanium as $Ti^{4+}$ or $TiO_2$. There are two other peaks with binding energies 457.3 and 464.4 eV, which can be associated to $Ti^{3+}$, associated to the interaction of titanium with sludge elements. Five peaks with binding energies of 283.7, 284.6, 285.4, 286.2, and 288.4 eV are visible in the XPS spectra of C 1s in FIG. 11 in (c), which can be associated with M-C, C—C, C—O, C═O and O—C—O, respectively. FIG. 11 in (d) shows XPS spectra of O1s with binding energies 530.1, 531.1, 532.2 and 533.4 eV, which can be ascribed to lattice oxygen, oxygen vacancies, adsorbed oxygen and adsorbed hydroxyl groups, respectively. FIG. 11 in (e) shows high-resolution XPS spectra of Si 2p with binding energies 96.1, 101.5, 103.3 and 105.9 eV. These peaks can be associated to Si, Si—C, Si—C—O and $SiO_2$, respectively. FIG. 11 in (f) shows the XPS spectra of Fe 2p with binding energies 691.9 and 693.7 eV, which can be ascribed to $Fe^{2+}$ and $Fe^{3+}$, respectively. FIG. 11 in (g) shows XPS spectra of Al 2p with binding energy 76.5 eV, which is linked to $Al_2O_3$. All these results confirm the presence of several metal elements in the sludge with their metallic state and would be useful to enhance photocatalytic efficiency. The wide spectrum in FIG. 11 in (h) is used to calculate the valance band position, which was estimated to be VB of 2.70 eV for $TiO_2$.

Figure 12:
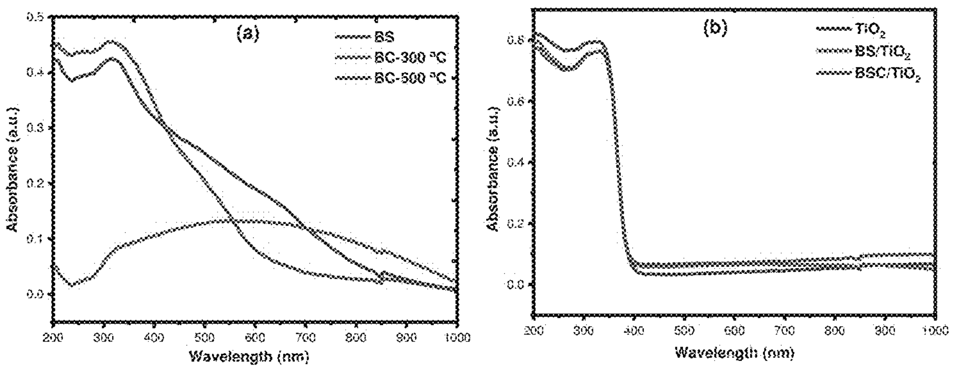
FIG. 12 depicts (a) UV-vis absorbance spectra of BS, BSC-300 and BSC-500 samples, (b) UV-vis absorbance spectra of $TiO_2$, BS/$TiO_2$ and BSC/$TiO_2$.

UV-Visible Absorption Investigation:

UV-visible absorption investigation was conducted to evaluate the light-harvesting capabilities of BS, BSC and their $TiO_2$-based nanocomposite materials and the results are shown in FIG. 12.

FIG. 12 in (a) shows UV-vis absorbance spectra of BS and BSC samples, synthesized at different temperatures. For the pure BS, a high absorbance is observed in the visible region. When the BS is heated at 300 and 500° C. to get BSC, the light absorbance trends are the same for the samples prepared at 500° C. However, in the case of BSC-300, higher light absorbance is obtained in the visible region.

FIG. 12 in (b) shows the light absorbance spectra of $TiO_2$ and BS/BSC-based $TiO_2$ composites. Pure $TiO_2$ has a wavelength of about 400 nm, which suggests a bigger band gap and can only absorb UV light with shorter wavelengths. In the case of BS/$TiO_2$ and BSC/$TiO_2$ samples, higher light absorbance can be observed in the visible light regions. However, there was no shift in bang gap energy with the loading of bio-sludge and biochar to $TiO_2$.

Photoluminescence (PL) Analysis:

Photoluminescence (PL) analysis is for evaluating electron-hole pair separation performance. In general, high electron-hole pair recombination performance is correlated with excessive photoluminescence strength, indicating a low photocatalytic activity.

Figure 13:
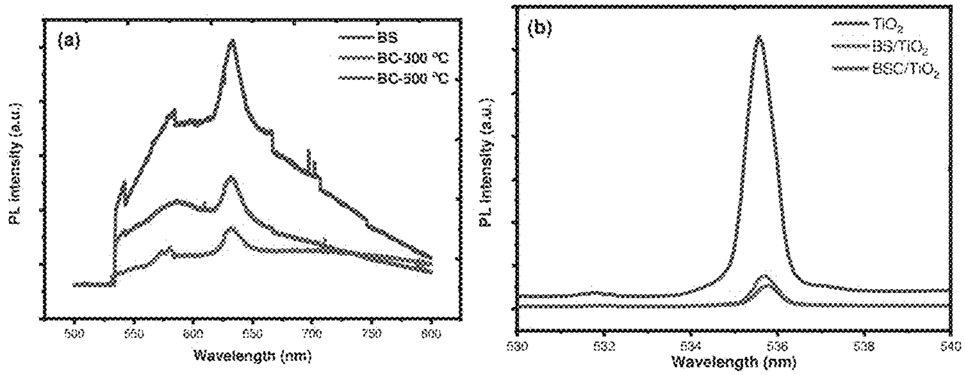
FIG. 13 depicts (a) Photoluminiscence (PL) analysis of bio-sludge and biochar prepared at different temperatures, (b) PL analysis of $TiO_2$, BS/$TiO_2$ and BSC/$TiO_2$ samples.

FIG. 13 in (a) shows the PL analysis of the pure materials such as BS, BSC-300 and BSC-500 samples. Notably, because of its conductive characteristics, pure BS, and BSC samples have a PL intensity that has very low intensity. Comparatively, the highest PL intensity was obtained using bio-sludge, which shows it has more potential to produce and recombine charge carriers. When the sludge is heated to a higher temperature, its PL intensity is decreased, which can be attributed to removing organic materials from the sludge and also because of activating metal elements inside the biochar.

FIG. 13 in (b) shows PL results of $TiO_2$, BS/$TiO_2$ and BSC/$TiO_2$ samples. The highest PL intensity was obtained for the $TiO_2$ due to more production and recombination of charge carriers. PL intensity is greatly decreased when BS is added to $TiO_2$ to create a BS/$TiO_2$ composite, which is undoubtedly caused by effective charge carrier separation. Similarly, when BSC is added to $TiO_2$, a further decrease in PL intensity is observed, which is due to removing sludge organics and producing biochar after heating the sludge. The decrease in photoluminescence intensity implies that long-lived transporters are present and that electron-hole detachment is successful. Charge separation is facilitated by the deposit of both bio-sludge and bio-char on $TiO_2$. Based on the presence of several metals. The sludge metals successfully reduce electron and hole recombination while promoting carrier lifetime.

Stability Analysis:

The stability of 3BS/$TiO_2$ and 3BSC/$TiO_2$ composites for photocatalytic $CO_2$ reduction to produce CO and $CH_4$ was further investigated to understand their practical applications. The performance of the 3BSC/$TiO_2$ composite was conducted for photocatalytic $CO_2$ reduction with methanol in multiple cycles and the results are presented in FIG. 14 in (a). In the first cycle, the highest CO production was obtained, however, it was decreased in the second cycle but its production was continuous in the remaining cycle. More interestingly, the production of $CH_4$ was lower in the first cycle but it was continuously increased in the consecutive cycles. In general, the production of CO and $CH_4$ was continuous after the $2^{nd}$ cycle, which confirms the stability of bio-sludge-derived biochar coupled with $TiO_2$.

Figure 14:
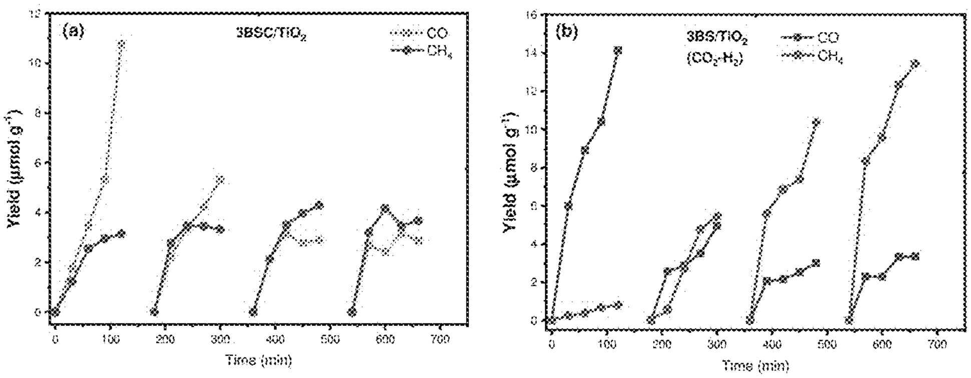
FIG. 14 depicts (a) Stability analysis of BSC/$TiO_2$ for the production of CO and $CH_4$ during $CO_2$ reduction with methanol in consecutive four cycles; (b) Stability analysis of BS/$TiO_2$ for the production of CO and $CH_4$ during $CO_2$ reduction with hydrogen in consecutive four cycles.

FIG. 14 in (b) shows the performance of the 3BS/$TiO_2$ composite for photocatalytic $CO_2$ reduction with $H_2$ to produce CO and $CH_4$. In the first cycle, the highest amount of CO is produced with a lower yield of $CH_4$. In the second cycle, the production of $CH_4$ was increased, whereas, the production of CO was decreased. In the next cycles until $4^{th}$ cycle, the production of $CH_4$ was continuous and the production of CO was slightly decreased. These results can be explained based on several possibilities and hypotheses. During the irradiation period, intermediate products and CO adhered to the catalyst surface, eventually reacting with hydrogen to produce methane. Another contributing factor could be the activation of metals within the bio-sludge, which helped prevent charge carriers and provided additional active sites. Previous observations indicated that the photostability of $V_2C$/g-$C_3N_4$ decreased when $CO_2$ was photo-reduced using $H_2O$/methanol to generate CO and $CH_4$. Similarly, during photocatalytic dry reforming of methane to create synthesis gas, a reduction in photostability was seen over the $V_2AlC$/g-$C_3N_4$ composite. Continuous and stable products were found when the $Ti_3AlC/TiO_2$ composite was evaluated for photocatalytic bi-reforming of methane, with CO and $H_2$ as possible products.

I claim:

1. A nanocomposite material comprising 2D/0D bio-sludge or biochar/$TiO_2$, wherein the nanocomposite material is supported on a support structure, wherein the bio-sludge or biochar comprises metal elements, and wherein the support structure comprises carbon nanotubes or a mesoporous material, or wherein the support structure is a substrate that comprises one or more of a ceramic, graphene, a metal, a metal oxide, a metal alloy, or a polymer.

2. The nanocomposite material as claimed in claim 1, wherein the nanocomposite material has a hierarchical porous nanotexture, and the bio-sludge or biochar is in layer form.

3. The nanocomposite material as claimed in claim 1, wherein the bio-sludge/biochar loading in the composite is from about 1 wt % to about 10 wt % to the total weight of the nanocomposite.

4. The nanocomposite material as claimed in claim 1, wherein the 0D $TiO_2$ particles are dispersed on the layers of the 2D bio-sludge or biochar.

5. The nanocomposite material as claimed in claim 1, which is prepared by a method that comprises combining the bio-sludge or biochar with $TiO_2$ by a sol-gel process and/or self-assembly of the particles through physical mixing.

6. A fixed bed photoreactor system, which comprises:

a reactor chamber comprising an inlet, an outlet, and a glass window for passing light irradiation; and a fixed bed of nanocomposite material comprising 2D/0D bio-sludge or biochar/$TiO_2$ disposed within the reactor chamber.

7. The fixed bed photoreactor system as claimed in claim 6, which further comprises:

a light source for producing light to enter the reactor chamber through the glass window.

8. The fixed bed photoreactor system as claimed in claim 6, which further comprises $CO_2$, $CH_4$, CO, water, and optionally one or more of $H_2$, methanol, ethanol, acetic acid, propanol, glycerol, or TEOA, within the reactor chamber.

9. The nanocomposite material as claimed in claim 1, wherein the bio-sludge/biochar loading in the composite is from about 1 wt % to about 5 wt % to the total weight of the nanocomposite.

10. The nanocomposite material as claimed in claim 1, wherein the bio-sludge/biochar loading in the composite is about 3 wt % to the total weight of the nanocomposite.

11. The nanocomposite material as claimed in claim 1, wherein the metal elements comprise two or more of Fe, Zn, Ni, Al, and Au.

* * * * *